US011389656B2

(12) United States Patent
Bonnet et al.

(10) Patent No.: US 11,389,656 B2
(45) Date of Patent: *Jul. 19, 2022

(54) ACTIVE IMPLANTABLE MEDICAL DEVICE FOR NERVE STIMULATION THERAPY WITH DYNAMIC ADJUSTMENT OF STIMULATION PERIODS

(71) Applicants: SORIN CRM SAS, Clamart (FR); UNIVERSITÉ DE RENNES 1, Rennes (FR); INSERM—INSTITUT NATIONAL DE LA SANTE ET DE LA RECHERCHE MEDICALE, Paris (FR)

(72) Inventors: Jean-Luc Bonnet, Massy (FR); Alfredo Hernandez, Cesson Sévigné (FR); Guy Carrault, Cesson Sévigné (FR); Hector Romero, Rennes (FR)

(73) Assignees: SORIN CRM SAS, Clamart (FR); UNIVERSI IÉ DE RENNES 1, Rennes (FR); INSERM—INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 165 days.

This patent is subject to a terminal disclaimer.

(21) Appl. No.: 16/229,281

(22) Filed: Dec. 21, 2018

(65) Prior Publication Data
US 2019/0126048 A1    May 2, 2019

Related U.S. Application Data

(63) Continuation of application No. 14/806,046, filed on Jul. 22, 2015, now Pat. No. 10,159,840.

(30) Foreign Application Priority Data

Jul. 23, 2014    (FR) ...................................... 1457109

(51) Int. Cl.
    A61N 1/36    (2006.01)
(52) U.S. Cl.
    CPC ..... A61N 1/36139 (2013.01); A61N 1/36053 (2013.01); A61N 1/36114 (2013.01); A61N 1/36146 (2013.01); A61N 1/36167 (2013.01)
(58) Field of Classification Search
    CPC ............ A61N 1/36139; A61N 1/36175; A61N 1/36114; A61N 1/36053
    See application file for complete search history.

(56) References Cited

U.S. PATENT DOCUMENTS 7,483,747 B2    1/2009  Gliner et al.
10,159,840 B2 * 12/2018  Bonnet .............. A61N 1/36146
(Continued)

FOREIGN PATENT DOCUMENTS

EP    2 019 714        2/2009
EP    2 092 885 A1     8/2009
(Continued)

OTHER PUBLICATIONS

Preliminary Search Report for French Patent Application No. 1457109, dated Jan. 7, 2015, 1 page.

*Primary Examiner* — George R Evanisko
(74) *Attorney, Agent, or Firm* — Foley & Lardner LLP

(57) ABSTRACT

An active implantable medical device for neurostimulation therapy is disclosed. The device produces stimulation pulse sequences generated continuously in succession during activity periods separated by intermediate inactivity periods during which no stimulation is issued. An input signal, provided by a physiological sensor, representative of cardiac activity and/or of the patient's hemodynamic status is received by circuitry. The circuitry further provides for dynamic control of the neurostimulation therapy, wherein the length of activity periods is modulated based on the current value level of the control parameter compared to a (Continued)

threshold. The duration of the next period of inactivity is calculated by the circuitry at the end of each activity period to maintain a constant duty cycle ratio between periods of activity and periods of inactivity.

20 Claims, 5 Drawing Sheets

(56) References Cited

U.S. PATENT DOCUMENTS

| | | |
|---|---|---|
| 2005/0197675 A1* | 9/2005 | David ................ A61B 5/4029 607/9 |
| 2006/0015153 A1 | 1/2006 | Gliner et al. |
| 2006/0122675 A1 | 6/2006 | Libbus et al. |
| 2007/0255374 A1 | 11/2007 | Kolafa et al. |
| 2011/0257708 A1 | 10/2011 | Kramer et al. |
| 2012/0172741 A1 | 7/2012 | Arcot-Krishnamurthy et al. |

FOREIGN PATENT DOCUMENTS

| | | |
|---|---|---|
| WO | WO-2007/127150 A1 | 11/2007 |
| WO | WO-2014/074523 A1 | 5/2014 |

\* cited by examiner

ACTIVE IMPLANTABLE MEDICAL DEVICE FOR NERVE STIMULATION THERAPY WITH DYNAMIC ADJUSTMENT OF STIMULATION PERIODS

CROSS-REFERENCE TO RELATED PATENT APPLICATIONS

This application is a Continuation of U.S. patent application Ser. No. 14/806,046, filed Jul. 22, 2015, which claims the benefit of and priority to French Patent Application No. 1457109, filed Jul. 23, 2014, both of which are incorporated herein by reference in their entireties.

BACKGROUND

The invention relates to "active implantable medical devices" as defined by the Directive 90/385/EEC of 20 Jun. 1990 of the Council of the European Communities.

It more specifically relates to devices that deliver pacing therapies of the nervous system, including vagus nerve stimulation ("VNS"). This type of stimulation may be referred to generally as "neurostimulation". The device includes for this purpose a lead with an electrode implanted on the vagus nerve and a generator delivering VNS pulses on this electrode.

Central nervous system stimulation therapy is recognized with respect to many disorders, such as epilepsy, pain, heart failure, apnea, obesity, etc. For the treatment of disorders such as heart failure, epilepsy or obesity, the devices typically include a lead with an electrode implanted on the vagus nerve (called "VNS lead") and a generator supplying VNS pulses on this electrode.

In some therapies, the VNS stimulation profile is composed of repetitive bursts or pulse trains produced during periods of "activity" or "ON periods" of a few tens of seconds, interspersed with periods of "inactivity" or "OFF periods" of a few minutes during which stimulation is no longer issued.

The vagus nerve may be stimulated synchronously with the heart rate, in which case the device includes methods for collecting myocardium depolarization waves, typical methods for collecting an ECG by a subcutaneous electrode, or an EGM by an electrode implanted on or in the myocardium.

The VNS stimulation is particularly well suited to the treatment of cardiac disorders, especially in patients at risk of heart failure, wherein the vagus nerve stimulation acts on cardiovascular functions by reducing the heart rate. This reduces the cardiac contractility and increases the duration of diastole, which may help reduce the development of cardiac remodeling which may lead to a worsening heart failure status.

Indeed, in a patient with heart failure, or in the post-myocardial infarction, sympathetic activity is excessive (hypertonic sympathetic state), with a rather depressed parasympathetic system, leading to a heart rate faster than normal.

The problem addressed by the invention is related to the fact that the efficiency of neuronal therapy by VNS stimulation, if it is effective at the beginning of its implementation, decreases rapidly, probably due to compensation phenomena coming from the formation of a physiological control loop.

Thus, if, for example, the heart rate (or RR interval) of the patient is measured just before and just after the triggering of the VNS stimulation (that is to say just before and just after the transition from OFF to ON), there is a significant decrease in heart rate, which reaches a maximum after about ten seconds. However, all things being equal, the frequency starts to gradually increase even as the VNS stimulation continues to be applied. After a few tens of seconds, slower heart beat obtained by the stimulation VNS is only from 80% to 60% of what it was originally (when the VNS stimulation had begun to be applied). However, if the VNS stimulation is stopped (transition from ON to OFF) then reactivated later (end of OFF period), the initial effectiveness is recovered, followed by the same gradual weakening of the effect of the therapy.

The continuous application of VNS stimulation is therefore of diminishing benefit and it is for this reason that the technique of ON and OFF alternating periods of stimulation is implemented.

Another aspect to be considered is that of deleterious events such as cough, apnea, ectopic ventricular contractions, or PVCs (Premature Ventricular Contractions), which may occur as secondary effects of VNS stimulation. If such symptoms occur, the VNS stimulation should be reduced so that the drawbacks of the latter do not outweigh the benefits.

Today, the durations of the ON and OFF periods are essentially empirically programmed by the practitioner. The practitioner must find a compromise between a sufficiently long ON period for the VNS stimulation is beneficial to the patient, while avoiding a prolonged stimulation does not produce deleterious effects such as the occurrence of cough, etc. In practice, the practitioner should follow patients over a long period so as to finely adjust the durations of ON and OFF periods to the best of each patient.

Procedures that could help practitioners program these parameters would be beneficial, particularly in the field of cardiac rhythm management, especially for patients experiencing heart failure. As explained above, the ON duration periods have a significant impact on changes in rhythmic and/or hemodynamic parameters.

SUMMARY

One object of the invention is first to provide a device to overcome the above drawbacks by automatic dynamic adjustment of the ON periods to maximize the benefit to the patient of the VNS stimulation and second, to avoid the occurrence of adverse events that may be induced by that VNS stimulation.

WO 2007/127150 A1 (EP 2019714 A1) proposes to avoid the phenomena of compensation, to change the VNS "therapeutic protocol" by modulation of the applied ON/OFF periods (keeping the same duty cycle ratio) periodically after a predetermined time, or on detection of an event such as external activation by the user or the practitioner, or a signal from a sensor. The protocols, including the durations of ON periods, however, are determined a priori, arbitrarily and are unrelated to a physiological parameter that reflects the patient's current status at a given time.

US 2006/0015153 A1 (U.S. Pat. No. 7,483,747 B2) proposes to recalculate from time to time the duration of ON and OFF periods at regular intervals or not, or randomly. However, this technique does not take into account the instantaneous effects of VNS therapy.

US 2012/172741 A1 proposes to recalculate the duration of the ON periods to take into account physiological modifications with slow dynamic, such as impedance variations, fibrosis or alteration of nerve tissue that may change over the long term the physiological response to VNS therapy. The proposed method implements a closed loop which continuously adapts the duty cycle ratio, but without any threshold consideration or absolute duration of the ON and OFF periods.

WO 2014/074523 A1 describes another VNS therapy system, operating according to a principle of modification of a "maintaining" therapy. This approach consists in defining a level of maintaining ON-OFF duty cycle ratio and to adapt it, but only during the periods wherein a predefined physiological event (e.g. a tachyarrhythmia) is detected. The adaptation is made by iteratively increasing the maintaining value of the duty cycle ratio, without reaching a maximum level which could produce undesirable effects.

Various embodiments of the invention virtually adapt in real time, and continuously (and not only during the detection of a particular event, like in the case of the WO 2014/074523 A1 cited above), both the ON and OFF periods for every VNS stimulation cycle according to a continuously measured physiological parameter representative of cardiac activity and/or of the patient's hemodynamic status. This parameter, which provides a direct indicator of the efficacy of VNS stimulation on the functions that are the subject of therapy, is used to directly control the application of the VNS pulses to maximize the benefit to the patient.

More specifically, various embodiments of the invention provide an implantable device for neurostimulation therapy by stimulation of the vagus nerve or of one of its branches, for example, in a manner disclosed in US2012/172744 A1 above. The device includes a generator capable of producing sequences of stimulation pulses continuously generated in succession during periods of activity separated by inactivity periods during which no stimulation is issued. The device further includes circuitry for receiving an input signal, provided by a physiological sensor, representative of the cardiac activity and/or the hemodynamic status of the patient implanted with the device, and outputting to the generator a control parameter of the current effectiveness of neurostimulation therapy. The circuitry further provides for dynamic control of the neurostimulation therapy, capable of modulating the duration of the periods of activity based on the current value level of the control parameter.

The circuitry may be adapted to modulate for each VNS stimulation cycle the duration of the activity period, and are further adapted to calculate, at the end of each activity period, the duration of the inactivity period depending on the duration of the previous period.

According to various advantageous subsidiary characteristics:

the circuitry may be adapted to modulate the duration of the activity periods by comparison of the control parameter with a predetermined threshold;

the circuitry may be capable of modulating the duration of the inactivity periods to maintain a constant duty cycle ratio between activity periods and inactivity periods;

the circuitry may be further capable of monitoring for each cardiac cycle the crossing of a threshold value by the current value level of the control parameter, and ending at each cardiac cycle the period of activity from the crossing this threshold;

the threshold may be a fixed predetermined threshold, or a dynamic threshold, the device then further including circuitry for calculating a threshold of the control parameter for each current activity period;

in the latter case, the threshold calculation includes calculating the threshold based on an extremum value of the control parameter achieved consecutively to the triggering of the current activity period;

the threshold calculation may be based on: the measured difference between i) a base value of the control parameter before the triggering of the current activity period and ii) the extremum value of the control parameter reached after the triggering of the current activity period; a base value of the control parameter before the start of the current activity period; and/or the extremum value of the control parameter reached after the triggering of the current activity period;

the device may further include circuitry for detecting the occurrence of deleterious events such as cough, ventricular extrasystoles and/or apnea, and inhibiting the triggering of a sequence of stimulation pulses by the generator in the event of occurrence of a harmful event; the circuitry further provides for a timing control adapted to unconditionally stop the generation of the stimulation pulse sequence after lapse of a predetermined period; and the neurostimulation therapy may be provided via stimulation of the vagus nerve.

Various embodiments of the invention further provide a method of providing neurostimulation therapy to a patient. The method includes initiating an inactivity period in which no stimulation is applied. The method further includes checking if conditions are met to allow the triggering of an activity period. The conditions may include the absence of cough events, the absence of apnea events, and the absence of ventricular ectopic beats. If the conditions are not met, the inactivity period is reactivated and maintained for a predetermined duration. If the conditions are met, an activity period is initiated in which stimulation is applied. The method further includes monitoring a physiological control parameter representative of the cardiac activity and/or the hemodynamic status of the patient. If the physiological control parameter falls below a predetermined threshold, the activity period is terminated and the duration of a subsequent inactivity period is calculated. If a maximum duration of the activity period is reached, the activity period is terminated and the duration of a subsequent inactivity period is calculated. The duration of the subsequent activity period is calculated to maintain a constant duty cycle ratio between the inactivity period and the activity period.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

An exemplary embodiment of the invention will now be described.

Regarding its software aspects, the invention may be implemented by appropriate programming of the controlling software of a known stimulator of the vagus nerve (VNS stimulator).

Such a pacemaker includes a programmable microprocessor provided with circuits for shaping and delivering stimulation pulses to implanted electrodes. It is possible to transmit to it by telemetry software stored in memory and executed to implement the functions of the invention which will be described below.

The adaptation of these devices to implement the functions of the invention is within the reach of a skilled-in-the-art person and will not be described in detail.

The method of the invention is implemented primarily by software, through appropriate algorithms performed by a microcontroller or a digital signal processor. For the sake of clarity, the various processing applied will be decomposed and schematized by a number of separate functional blocks in the form of interconnected circuits, but this representation, however, is only illustrative, these circuits including common elements in practice corresponding to a plurality of functions generally performed by the same software.

Figure 1:
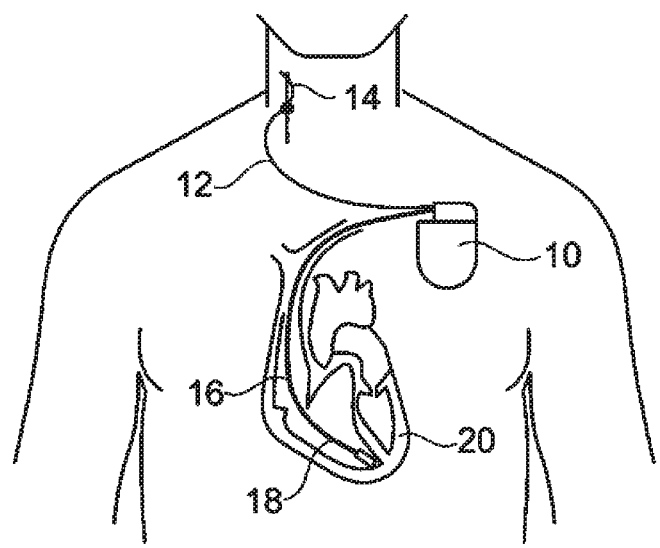
FIG. 1 is a schematic representation of the various elements implemented by the device of the invention, placed in context.

In FIG. 1, a system is illustrated including an implantable VNS generator 10 ensuring the production of stimulation pulses transmitted by a lead 12 to an electrode applied on the vagus nerve 14 or disposed proximate thereto or to one of its branches. The generator 10 is also provided with a cardiac lead 16 provided at its distal end 18 of an electrode for collecting the electrical activity of the myocardium 20. The lead 16 collects the endocardial electrogram signals (EGM) that will deliver a signal representative of the patient's cardiac activity, in the present case, the heart rate, determined by the duration of RR intervals of the successive cardiac depolarizations.

It must be noted that this method for collecting a signal representative of the patient's cardiac activity is not limiting, and it is possible to use other signals for the implementation of the invention, alternatively or in addition. Endocardial acceleration (EA) signals in particular may be used, which allow to obtain a parameter representative of the patient's hemodynamic status, e.g. the parameters described in EP 2092885 A1 (Sorin CRM S.A.S) such as the peak-to-peak amplitude of the first peak of endocardial acceleration (PEA 1), the interval between the first and second EA peak, etc.

In general, the received signal is intended to deliver a control parameter of the instantaneous efficiency of VNS therapy to a generator, this control parameter being possibly derived from signals delivered by other types of physiological sensors than those illustrated in this example, for example a blood pressure sensor, a minute ventilation sensor, etc.

The choice of the RR interval as the control parameter in the following description should not be considered in any way limiting of the invention.

Figure 2:
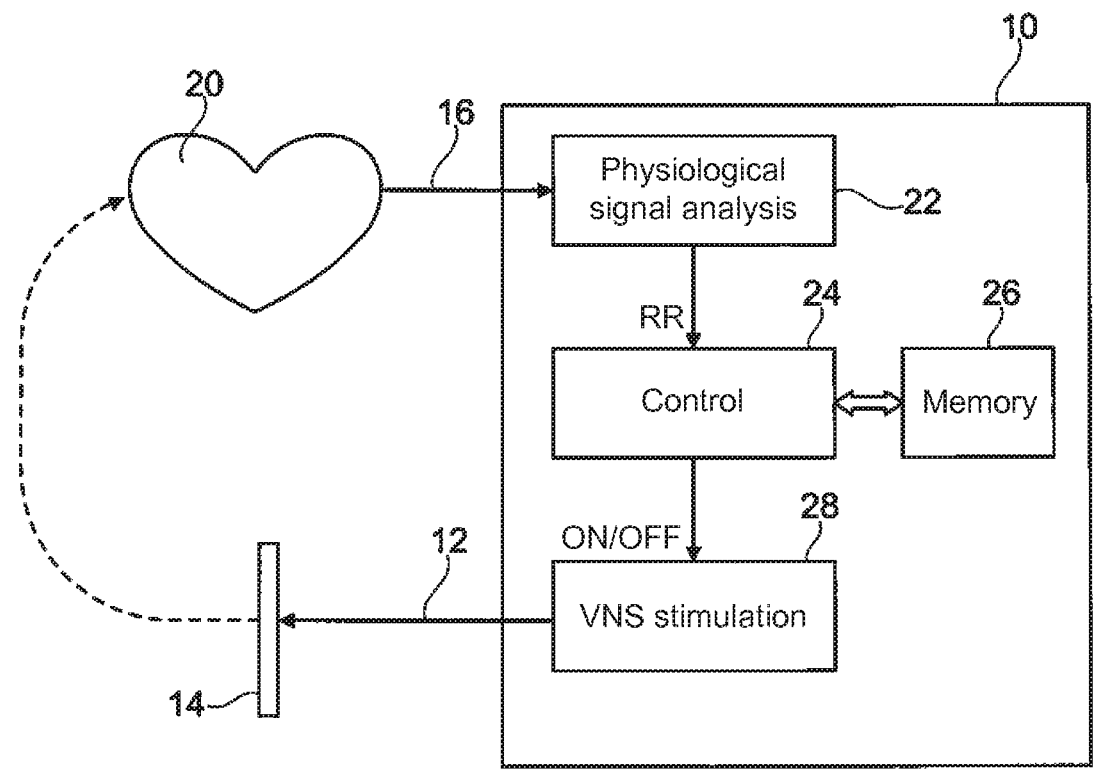
FIG. 2 illustrates in block diagram form the various functions implemented by the device of the invention.

FIG. 2 illustrates in block diagrams the various functions implemented by the device of the invention.

The pulse signal (EGM signal, EA signal, etc.) collected by the lead 16 is scanned (block 22) so as to output a control parameter of the instantaneous efficiency of VNS therapy, the parameter being in this example the heart rate, reflected in the value of successive RR intervals.

This control parameter is applied to a control unit (block 24) connected to a memory 26 in which various settings and thresholds are stored, the memory 26 keeping a history of triggers and stops of the VNS stimulation phases. The control unit 24 drives a pulse generator 28, selectively during periods of activity (ON periods) separated by intermediate periods of inactivity (OFF periods) during which no electrical stimulation is delivered to the vagus nerve 14 via the lead 12.

A VNS stimulation produces on heart activity a number of effects, such as:

Chronotropic effect: decreased heart rate, that is to say an increase in RR intervals;

Dromotropic effect: decreased AV conduction velocity, leading to an increase in P-R intervals;

Bathmotropic effect: decreased excitability of myositis;

Inotropic effect: cardiac contractility reduction; and/or

Lusitropic effect: increased cardiac relaxation speed.

VNS stimulation also has an effect on the vascular system by modulation of the vasoconstriction, with a change of the diameters of the arteries and of the peripheral resistance resulting in systemic vasodilation of the vasculature.

Figure 3:
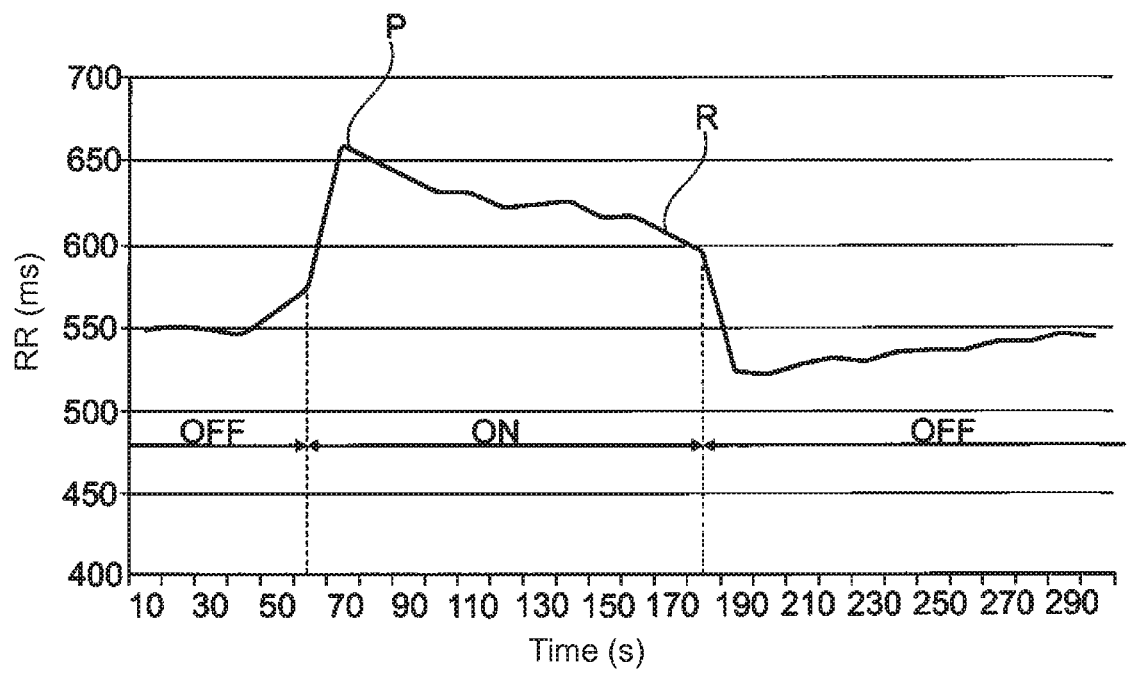
FIG. 3 illustrates the effect of the application of a VNS pulse burst on heart rate, an effect here reflected by variation of the RR interval.

Referring to FIG. 3, which represents the variation of the RR interval during alternating periods OFF/ON/OFF in a patient (everything else being equal), it is found that the chronotropic response to a VNS stimulation, as reflected by changes in heart rate (RR interval) results in four successive phases when VNS stimulation is applied. That is to say after a transition from an OFF period to an ON period:

A rapid increase in the RR interval, to a peak P;

After the peak P, a pseudo-plateau phase with progressive reduction of the RR interval (region marked R in FIG. 3);

At the stop of the VNS stimulation (that is to say the transition from ON to OFF), a rapid reduction in the RR interval, that is to say acceleration of the heart rate; and Finally, a recovery or "bounce" phase, which reflects the transient baroreflex responses leading to a final stabilization of blood pressure and of heart rate to the value they had before the application of VNS stimulation.

These four phases can also be observed on the inotropic response (variation of cardiac contractility) and on other types of responses, optionally with a slower dynamics due to larger time constants. It is for this reason that one preferably chooses, but is not limited to, analyzing the cardiac rhythm, in particular reflected by the variation of the RR interval as the control parameter of the instantaneous efficiency of the therapy VNS.

Figure 4:
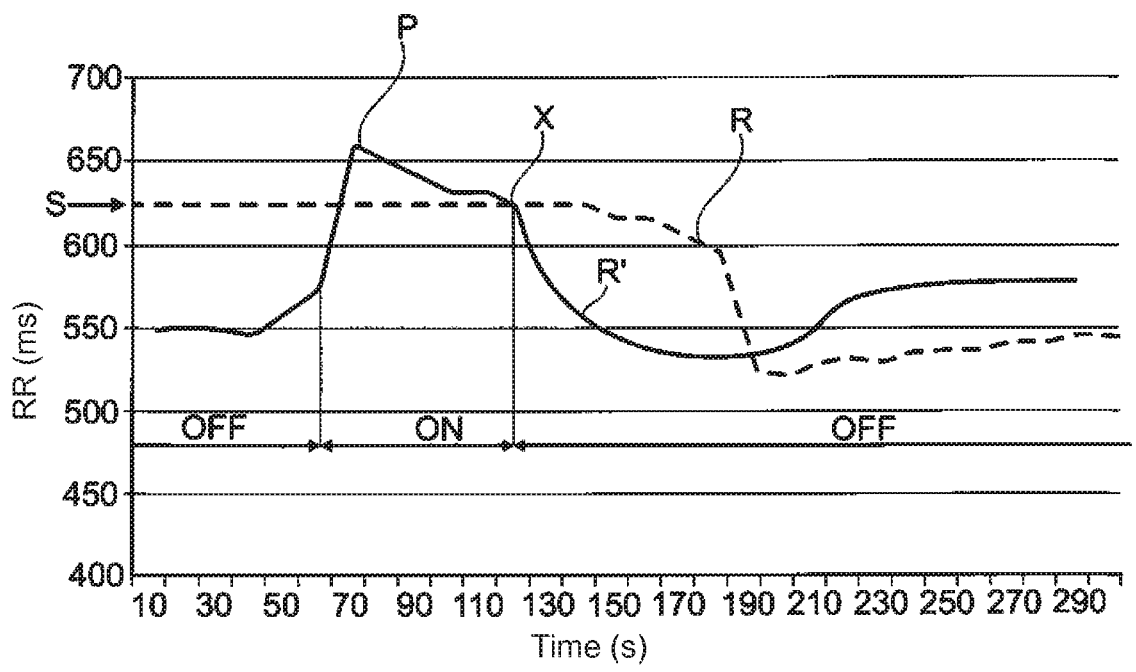
FIG. 4 is homologous to FIG. 3, showing the effect of VNS stimulation following the implementation of the invention.

As shown in FIG. 4, typically of the invention, the onset of the OFF period is controlled for each VNS stimulation cycle to shorten the ON period when the effect of VNS stimulation falls below a predetermined threshold.

To this end, the current value of the RR interval is compared with a threshold S, and when this threshold is crossed (point X in FIG. 4) VNS stimulation is stopped, that is to say that a transition from an ON to an OFF period is triggered. The RR interval then decreases rapidly (curve R'), much faster than in the previous case of FIG. 3 (shown in dashed line R in FIG. 4).

This technique allows dynamic adaptation of the VNS stimulation from one patient to another and from one moment of the day to another for the same patient, in order to avoid applying therapy for too long, producing too few positive effects for the patient. Optimally, the transition from the ON period to the OFF period is tested and optionally triggered at each VNS stimulation cycle.

Figure 5A:
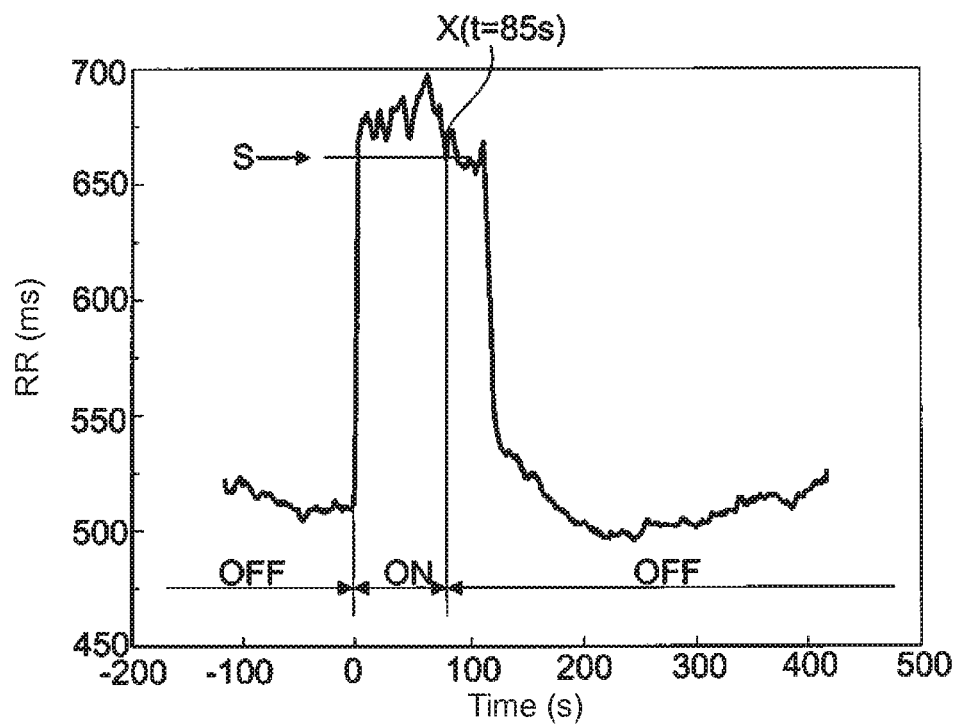
FIGS. 5a and 5b are timing diagrams for two different patients identified in a clinical study showing the changes in heart rate reflected by the variation of the RR interval following application of a VNS therapy according to the teachings of invention.
Figure 5B:
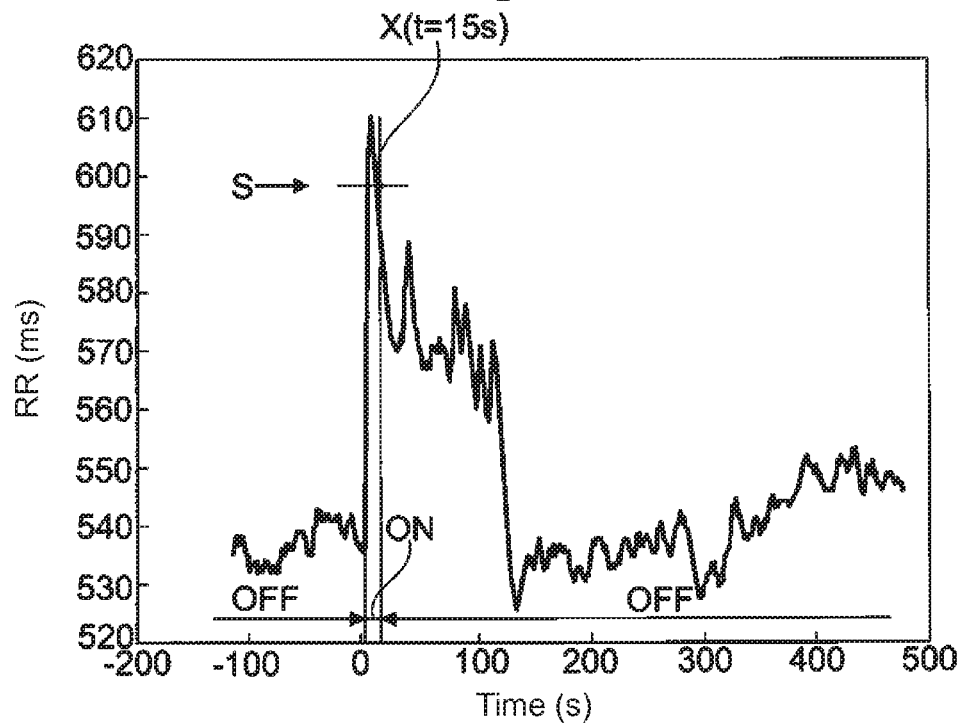

FIGS. 5a and 5b show variations in the RR interval for two different patients collected in the course of a clinical study.

We see that for the patient in FIG. 5a VNS stimulation produced positive effects for a relatively long time from the moment it is applied, the threshold S being crossed after about t=85 seconds. By contrast, for the patient of FIG. 5b, the effectiveness of the stimulation decreases very quickly after the peak has been reached, so it is not necessary to extend the therapy too long. In this case the threshold S is crossed after t=15 seconds and VNS stimulation is not extended beyond.

In a first embodiment, the threshold S is a fixed threshold with respect to the value of the RR interval reached at the peak P, for example a threshold S set at 20 milliseconds below the level of the peak P.

In another embodiment, the interval between the threshold and the peak value is variable, for example defined by a percentage of the difference between the base value of the RR interval (mean value calculated over a certain number of cycles during the OFF period just before the transition to the ON period) and the value of the RR interval corresponding to the peak reached after the transition from the OFF period to the ON period. The threshold may for example be calculated as being equal to 25% of the difference between the base RR value and the peak RR value. In the example shown in FIG. 4, if the peak value is 660 ms and the base value is 550 ms, the threshold will be defined as: (660-550)× 0.25=27.5 ms below the peak value.

In yet another embodiment, the threshold S can be calculated from the sole base RR value, or the sole RR peak value.

Advantageously, the method of the invention, after having dynamically ended VNS stimulation, adapts the duration of the OFF period, depending on the length of the ON period which has just been controlled.

The calculation of the OFF period is advantageously made by choosing to retain a constant duty cycle ratio, that is to say, a constant ratio between the ON periods and that of the ON+OFF periods. For example, if the duty cycle ratio is fixed at 1:4, the duration of the OFF period will be three times the duration of the ON period immediately preceding it.

Figure 6:
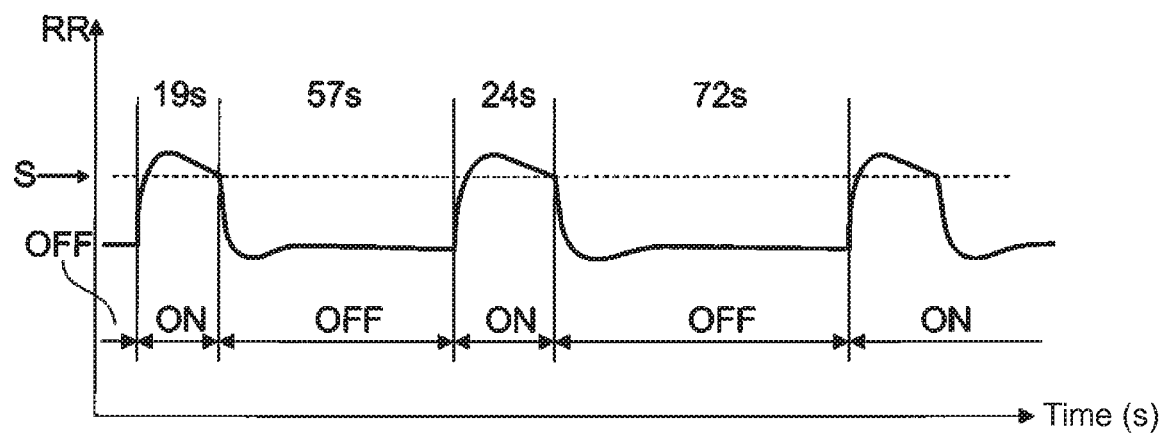
FIG. 6 illustrates, for three cycles of VNS stimulation, the interconnected variations of the ON and OFF period durations.

In FIG. 6, an example of three consecutive ON periods separated by OFF periods is illustrated. The first ON period was interrupted after 19 s, and the duration of the next OFF period will be calculated at the end of the ON period according to the duration of this period, that is 19×3=57 s. For the following ON period which will be stopped after 24 s, the duration of the subsequent OFF period is 24×3=72 s, and so on. The ON:OFF duty cycle ratio can be selected from any value in the range [0%-100%].

Figure 7:
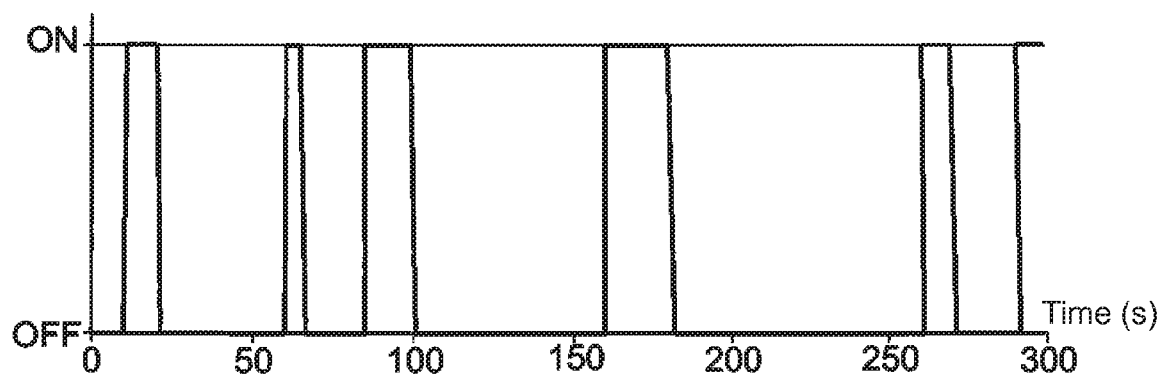
FIG. 7 illustrates the alternation of the variables ON and OFF periods, in time.

As shown in FIG. 7, a series of ON periods of varying length, followed by OFF periods of also varying length, but with a maintained constant duty cycle ratio, is observed over time.

Figure 8:
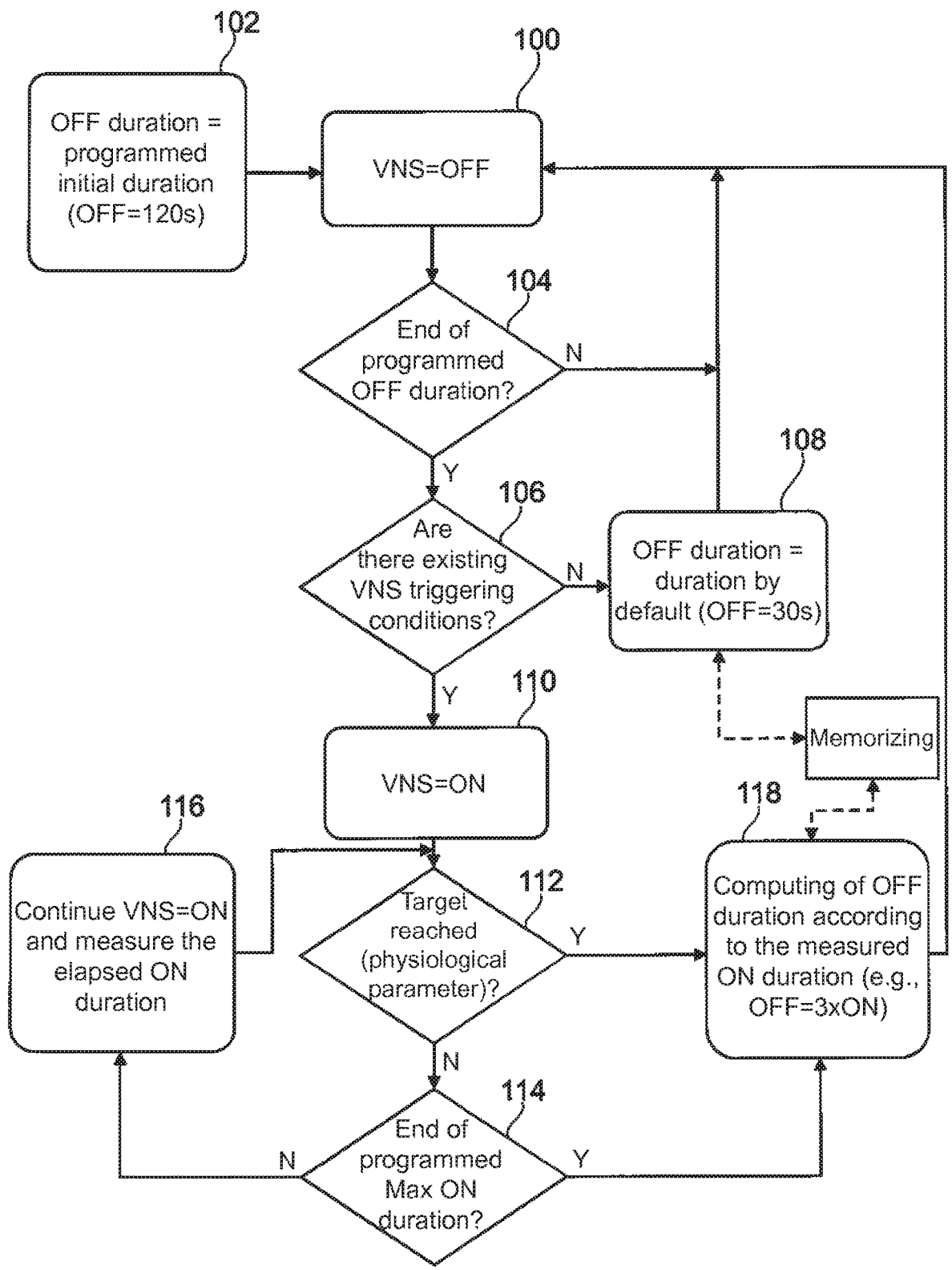
FIG. 8 is a general flow chart showing the sequence of steps for the implementation of a VNS stimulation device according to the invention.

FIG. 8 is a flowchart showing the progress of the different steps of the method of the invention.

Initially the device is in a configuration wherein no VNS stimulation is applied (VNS=OFF, block 100), the OFF period being adjusted to a predetermined initial duration (block 102). This value can be either a value programmed by the doctor, for example 120 seconds, or a value calculated by the device based on patient history.

At the end of the initial period (block 104), the device checks (block 106) if the conditions are met to allow the triggering of a VNS stimulation. The device controls in particular the absence of cough or apnea events (e.g., by analyzing the minute ventilation signal), the absence of ventricular ectopic beats (by analyzing the EGM signal), etc.

If any of these phenomena is present, the OFF period is maintained and reactivated for a predetermined duration, for example 30 seconds (block 108).

In the absence of a phenomenon preventing the issuance of a VNS therapy, stimulation is applied (VNS=ON, block 110) and the physiological control parameter, such as RR interval, is constantly monitored.

If the predefined target is reached, for example if the RR interval falls below a predetermined threshold (block 112), then the duration of the subsequent OFF period is calculated to maintain a constant duty cycle ratio (e.g. OFF=3×ON) (block 118) and the VNS stimulation is terminated (transition to an OFF period, back to block 100).

Otherwise, if a maximum pre-programmed duration is reached (block 114) then in the same method, the duration of the OFF period that follows is calculated and the VNS stimulation is stopped (blocks 118, 100). If the pre-programmed duration is not reached yet, the VNS stimulation is continued (block 116) and the method returns to block 112 of monitoring of the threshold crossing.

What is claimed is:

1. A method of providing neurostimulation therapy to a patient, the method comprising:
   checking if conditions are met to allow initiation of an activity period during which stimulation is applied to the patient;
   initiating the activity period in response to the conditions being met;
   monitoring a physiological control parameter representative of at least one of cardiac activity or a hemodynamic status of the patient, wherein a base value of the physiological control parameter is monitored before the activity period and a peak value of the physiological control parameter is monitored during the activity period;
   calculating a threshold value for the physiological control parameter based on the peak value or based on a subtraction of the base value from the peak value; and
   terminating the activity period in response to a first of the physiological control parameter falling below the threshold value or a maximum duration of the activity period being reached.

2. The method of claim 1, further comprising calculating a duration of an inactivity period during which no stimulation is generated subsequent to the activity period.

3. The method of claim 2, wherein calculating the duration of the subsequent inactivity period comprises calculating the duration of the subsequent inactivity period to maintain a constant duty cycle ratio between the inactivity period and the activity period.

4. The method of claim 3, wherein the constant duty cycle ratio is that the duration of the inactivity period is three times a duration of the activity period.

5. The method of claim 2, further comprising initiating the inactivity period subsequent to the termination of the activity period.

6. The method of claim 5, further comprising:
after the duration of the inactivity period, checking if the conditions are met to allow initiation of a second activity period during which stimulation is applied to the patient; and
activating a second inactivity period during which no stimulation is generated in response to the conditions not being met.

7. The method of claim 6, further comprising maintaining the second inactivity period for a predetermined duration.

8. The method of claim 1, wherein the stimulation is provided via stimulation of a vagus nerve of the patient.

9. The method of claim 1, wherein checking if the conditions are met comprises checking for an absence of at least one of a cough, an apnea event, or ventricular ectopic beats.

10. The method of claim 1, wherein the physiological control parameter is an RR interval.

11. An active implantable medical device for providing neurostimulation therapy to a patient, the active implantable medical device comprising:
a generator configured to produce the neurostimulation therapy comprising stimulation generated during activity periods separated by inactivity periods during which no stimulation is generated; and
circuitry configured to:
check if conditions are met to allow initiation of an activity period;
initiate the activity period in response to the conditions being met;
monitor a physiological control parameter representative of at least one of cardiac activity or a hemodynamic status of the patient, wherein a base value of the physiological control parameter is monitored before the activity period and a peak value of the physiological control parameter is monitored during the activity period;
calculate a threshold value for the physiological control parameter based on the peak value or based on a subtraction of the base value from the peak value; and
terminate the activity period in response to a first of the physiological control parameter falling below the threshold value or a maximum duration of the activity period being reached.

12. The device of claim 11, wherein the circuitry is further configured to calculate a duration of an inactivity period subsequent to the activity period.

13. The device of claim 12, wherein the circuitry is configured to calculate the duration of the subsequent inactivity period to maintain a constant duty cycle ratio between the inactivity period and the activity period.

14. The device of claim 13, wherein the constant duty cycle ratio is that the duration of the inactivity period is three times a duration of the activity period.

15. The device of claim 12, wherein the circuitry is further configured to initiate the inactivity period subsequent to the termination of the activity period.

16. The device of claim 15, wherein the circuitry is further configured to:
after the duration of the inactivity period, check if the conditions are met to allow initiation of a second activity period during which stimulation is applied to the patient; and
activate a second inactivity period during which no stimulation is generated in response to the conditions not being met.

17. The device of claim 16, wherein the circuitry is further configured to maintain the second inactivity period for a predetermined duration.

18. The device of claim 11, wherein the active implantable medical device is configured to provide the stimulation to a vagus nerve of the patient.

19. The device of claim 11, wherein the circuitry is configured to check if the conditions are met by checking for an absence of at least one of a cough, an apnea event, or ventricular ectopic beats.

20. The device of claim 11 wherein the physiological control parameter is an RR interval.

* * * * *